US011576712B1

(12) United States Patent
Belle et al.

(10) Patent No.: US 11,576,712 B1
(45) Date of Patent: Feb. 14, 2023

(54) SYSTEM AND METHOD FOR NON-INVASIVE FAT REDUCTION

(71) Applicants: Elizabeth Belle, Little Rock, AR (US); Rita Diane Ellis, St. Louis, MO (US)

(72) Inventors: Elizabeth Belle, Little Rock, AR (US); Rita Diane Ellis, St. Louis, MO (US)

( * ) Notice: Subject to any disclaimer, the term of this patent is extended or adjusted under 35 U.S.C. 154(b) by 0 days.

(21) Appl. No.: 17/552,185

(22) Filed: Dec. 15, 2021

Related U.S. Application Data

(60) Provisional application No. 63/126,090, filed on Dec. 16, 2020.

(51) Int. Cl.
*A61B 18/02* (2006.01)
*A61B 18/00* (2006.01)
*A61F 7/00* (2006.01)

(52) U.S. Cl.
CPC ............ *A61B 18/0206* (2013.01); *A61B 2018/00005* (2013.01); *A61B 2018/00464* (2013.01); *A61B 2018/00714* (2013.01); *A61B 2018/00791* (2013.01); *A61B 2018/00994* (2013.01); *A61B 2018/0237* (2013.01); *A61B 2018/0262* (2013.01); *A61F 2007/0075* (2013.01)

(58) Field of Classification Search
CPC ........... A61B 18/02; A61B 18/0206; A61B 2018/0262; A61B 2018/00005; A61B 2018/00023; A61B 2018/00452; A61B 2018/00047; A61B 2018/00291; A61B 2018/00464; A61B 2018/00458; A61B 2018/00994; A61B 2018/0225; A61B 2018/0237; A61B 2018/0243; A61B 2007/0008; A61B 2007/0034; A61B 2007/0078; A61F 2007/0075; A61N 7/00
USPC ...... 606/20, 22, 23, 25, 26; 607/96, 104, 108
See application file for complete search history.

(56) References Cited

U.S. PATENT DOCUMENTS

| | | | |
|---|---|---|---|
| 6,500,141 B1 * | 12/2002 | Irion | A61N 7/00 604/20 |
| 2008/0195000 A1 * | 8/2008 | Spooner | A61H 23/0245 601/2 |
| 2015/0283022 A1 * | 10/2015 | Lee | A61N 1/40 601/2 |

* cited by examiner

*Primary Examiner* — Thomas A Giuliani
(74) *Attorney, Agent, or Firm* — Schrantz Law Firm, PLLC; Stephen D. Schrantz

(57) ABSTRACT

The cooling system cools a patient's tissue while applying suction to the skin and applying ultrasound waves to the tissue to reduce fat cells. The cooling applicator simultaneously provides suction, cooling, and ultrasound to the treatment area of the patient. The applicator connects to a suction to draw the tissue longitudinally into a cavity of the applicator. Cooling plates located laterally outward from the cavity cool the tissue during the treatment. A transducer located longitudinally above the cavity transmits ultrasound waves longitudinally downward into the cavity and the tissue. The ultrasound provides non-focused treatment such that the transducer transmits the ultrasound waves oriented horizontally and vertically longitudinally downward at the tissue. A treatment pad placed on the patient's skin directly contacts the patient such that the applicator does not directly contact the patient. The treatment pad is constructed from a fabric storing a glycerin gel, deionized water, and fructose.

16 Claims, 6 Drawing Sheets

SYSTEM AND METHOD FOR NON-INVASIVE FAT REDUCTION

CROSS-REFERENCE TO RELATED APPLICATIONS

This application is a continuation in part of U.S. Patent Application No. 63/126,090 filed on Dec. 16, 2020 entitled System and Method for Non-Invasive Fat Reduction which is hereby incorporated by reference.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

I. Field of the Invention

The invention relates to a device, system, and technique for reducing and/or eliminating fat cells. The present invention relates to ultrasound assisted cooling technology to reduce and/or eliminate fat cells. More specifically, the present invention provides a non-invasive device, system, and technique for reducing body fat and temporarily reducing cellulite in the targeted abdominal area.

II. Description of the Known Art

Patents, patent applications, and references disclosing relevant information are disclosed below. These patents, patent applications, and references are hereby expressly incorporated by reference in their entirety.

U.S. Pat. No. 10,806,500 issued to DeBenedictis on Oct. 20, 2020 ("the '500 patent") teaches treatment systems, methods, and apparatuses for improving the appearance of skin or other target regions. Aspects of the technology taught by the '500 patent are directed to improving the appearance of skin by tightening the skin, improving skin tone or texture, eliminating or reducing wrinkles, increasing skin smoothness, or improving the appearance of cellulite. Treatments taught by the '500 patent can include cooling a surface of a patient's skin and detecting at least one freeze event in the cooled skin. The treatment system taught by the '500 patent can continue cooling the patient's skin after the freeze event(s) are detected so to maintain at least a partially frozen state of the tissue for a period of time.

SUMMARY OF THE INVENTION

The present invention applies ultrasound assisted cooling technology to reduce fat cells. The present invention provides a control unit having a controller, at least one cooling applicator (preferably two applicators) with a display, and a treatment pad for thermal coupling for the patient.

The system is indicated for cryolipolysis of the abdomen in individuals with a Body Mass Index (BMI) of 30 or less. The system is intended to affect the appearance of the abdomen via cryolipolysis. The system is intended for use by a trained physician or a physician-designated medical professional.

The control unit of one embodiment is a portable device, such as a housing, that houses the user interface, the cooling device, and the controller. The controller controls the cooling device within the applicator. Sensors monitor the temperature of the cooling devices within the applicator. The system alerts the operator if the cooling devices deviate from the target temperature with an audible alert, a visual alert, or both an audible and visual alert.

The control unit connects to a power source. The power source powers the controller and the applicators. An isolation transformer isolates the electrical components of the system. The system enables simultaneous use of two applicators that provide ultrasound and cooling simultaneously.

In one embodiment, the operator activates/deactivates the applicators via a display, such as an LCD screen, or other controls on the control unit or the applicators. Sensors on the applicators monitor the temperatures, pressure, and ultrasound applied by the applicators to the patient. The sensors monitor that the treatment is being properly applied to the patient. Upon reaching the end of the treatment, the controller shuts the applicators down to terminate the treatment.

The system provides two applicators for treating the patient. The applicators simultaneously provide suction, cooling, and ultrasound to the treatment area of the patient. Such treatment breaks down fatty tissue of the patient for the body to absorb the fatty tissue.

The applicators draw the patient's tissue at the treatment area into the applicator. Cooling devices within the applicator cool the tissue. Sensors monitor the temperature of the tissue during the cooling process. The cooling device of one embodiment provides cooling plates constructed from aluminum.

The applicators also provide transducers to apply ultrasound to the treatment area of the patient. The applicators apply ultrasound to the tissue drawn into the applicator. The ultrasound provides non-focused treatment such that the ultrasound waves are oriented in a first orientation and a second orientation that are not parallel. In one embodiment, the ultrasound waves are oriented horizontally and vertically. In one embodiment, the second orientation is perpendicular to the first orientation.

The applicator of one embodiment does not directly contact the patient. A treatment pad placed on the patient's skin directly contacts the patient. The treatment pad and the patient's tissue are drawn into the applicator when treating the patient. The treatment pad is constructed from a fabric storing a glycerin gel that is soaked in deionized water and fructose. The treatment pad facilitates thermal contact and mitigates minor thermal variations.

Accordingly, it is an object of the present invention to reduce fat cells in a patient.

It is another object of the present invention to provide an applicator that both cools the tissue and applies ultrasound to the tissue within a single applicator.

It is another object of the present invention to provide an applicator that simultaneous provides pressure to the tissue via suction, cools the tissue, and applies ultrasound to the tissue.

It is another object of the present invention to apply non-focused ultrasound to the tissue.

It is another object of the present invention to apply ultrasound waves in first orientation and a second orientation that are not parallel to each other to the tissue being treated.

It is another object of the present invention to apply ultrasound waves in first orientation and a second orientation that are perpendicular to each other to the tissue being treated.

These and other objects and advantages of the present invention, along with features of novelty appurtenant thereto, will appear or become apparent in the course of the following descriptive sections and the attached drawings.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION

Figure 1:
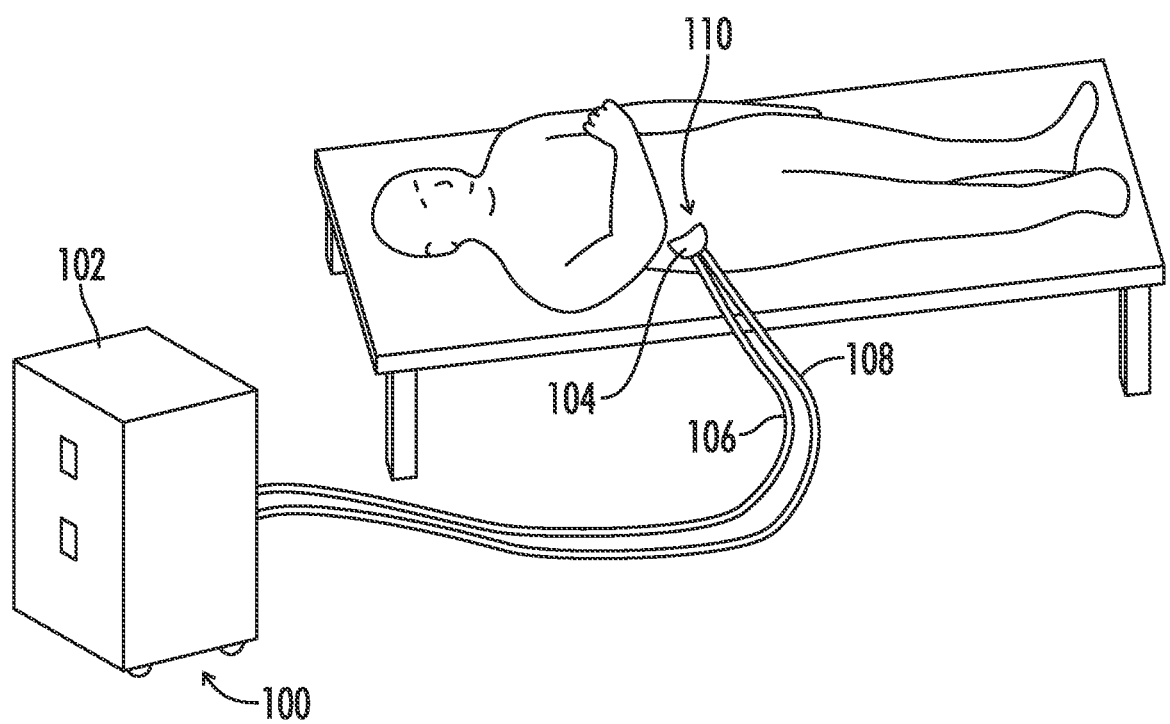
FIG. 1 is an environmental view of one embodiment of the present invention.

FIG. 1 shows the treatment system 100 for applying ultrasound assisted cooling technology to reduce fat cells. The system 100 provides a control unit having a controller, at least one cooling applicator 104 (preferably two applicators) with a display, and a treatment pad for thermal coupling with the patient.

The applicator 104 treats a patient 110 to reduce fat cells within tissue of the patient 110. The system 100 provides two applicators 104 for treating the patient 110. The applicators 104 simultaneously provide suction, cooling, and ultrasound to the treatment area of the patient 110. Such treatment breaks down fatty tissue of the patient 110 for the body to absorb the fatty tissue.

The applicator connects to a portable device, such as housing 102, that houses a chiller, a fluid reservoir, and a suction receptacle. The housing 102 is also connected to a controller, a pump for transferring fluid from the receptacle to the applicator 104, and a suction to be applied at the applicator 104.

Suction of the applicators 104 draw the patient's tissue at the treatment area into the applicator 104. In one embodiment, the suction pump is stored within the housing 102. The suction draws tissue into the applicator 104 for treatment.

The suction connects to the applicator 104 via conduit 106. Any debris, fluids, or other materials drawn into the applicator 104 travel through conduit 106 to a filter where the debris, fluids, or other materials are deposited into suction reservoir within housing 102.

The suction draws the tissue into the applicator 104. The pressure of the suction of one embodiment ranges from −250 kPa to −750 kPa, preferably −500 kPa. Such suction draws the tissue into the applicator 104 and applies force on the tissue to increase the breakdown of fat within the tissue. At least one or more sensors within the applicator identify the pressure applied by the suction. The controller may then modify the suction to provide the appropriate suction.

Cooling elements within the applicator 104 cool the tissue. The cooling elements of one embodiment provide cooling plates constructed from aluminum. The cooling elements cool at a temperature ranging from −15 degrees Celsius to +10 degrees Celsius, preferably −11 degrees Celsius to +5 degrees Celsius. The cooling plates are thermoelectrically cooled. Electricity is provided to the plates through conduit 108. The thermoelectric effect cools the inner side of the cooling element closest to the tissue, while heating the outer side of the cooling element. As discussed above, the thermoelectric effect cools the inner side of the cooling element, such as the aluminum cooling plate, to a temperature ranging from −15 degrees Celsius to +10 degrees Celsius, preferably −11 degrees Celsius to +5 degrees Celsius.

At least one sensor at the applicator 104 monitors the temperature of the tissue during the cooling process. The sensor warns the operator if the temperature varies from the desired treatment temperature. In one embodiment, the treatment cools the tissue to −5 degrees Celsius for forty five (45) minutes.

To maintain the temperature, the system 100 cools the outer side of the cooling element with a heat sink. In one embodiment, a fluid, such as water, cools the outer side of the cooling element. The water flows across or adjacent the outer side of the cooling element. A pump within housing directs water from the water reservoir through a chiller to the cooling element. The chilled water flowing to the cooling element cools the cooling element.

The applicators 104 also provide transducers to apply ultrasound to the treatment area of the patient. In one embodiment, conduit 108 also powers the ultrasound. In another embodiment, a separate conduit powers the ultrasound. The applicators apply ultrasound to the tissue drawn into the applicator. The ultrasound provides non-focused treatment such that the ultrasound waves are oriented in a first orientation and a second orientation that are not parallel. In one embodiment, the second orientation is perpendicular to the first orientation. In another embodiment, the ultrasound waves are applied both horizontally and vertically through the transducers.

The applicator 104 of one embodiment does not directly contact the patient. A treatment pad placed on the patient's skin directly contacts the patient. The treatment pad and the patient's tissue are drawn into the applicator when treating the patient. The treatment pad is constructed from a fabric storing a glycerin gel that is soaked in deionized water and fructose. The treatment pad facilitates thermal contact and mitigates minor thermal variations.

Figure 2:
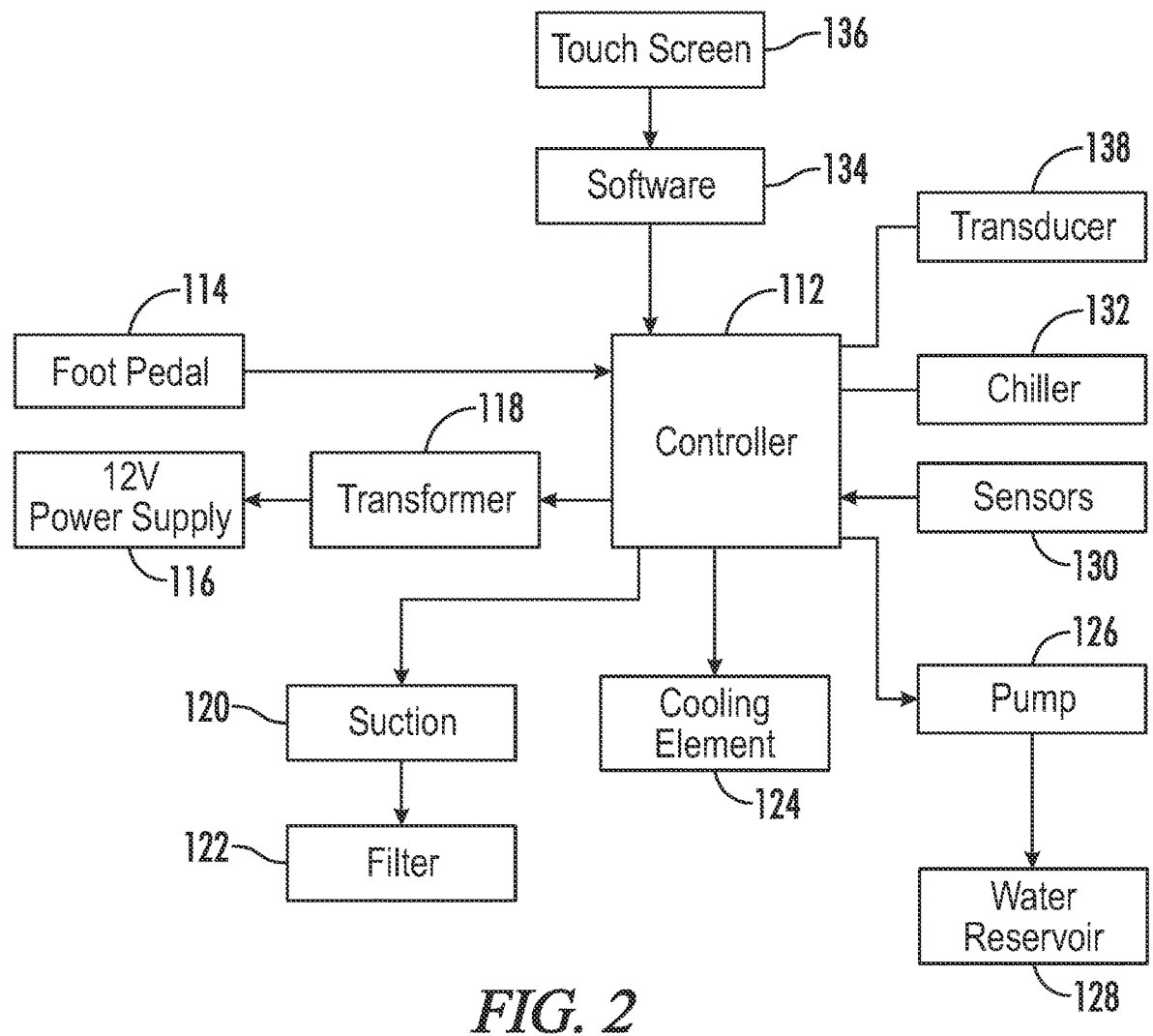
FIG. 2 is a schematic view of one embodiment of the present invention.

FIG. 2 shows the controller 112 for operation of the system. The controller 112 controls operation of the suction 120 that draws the tissue into the applicator. The suction 120 deposits any debris, fluid, or other materials drawn into the applicator 104 to a receptacle at the filter 122. The controller 112 operates the suction 120 at the proper pressure for drawing the tissue into the applicator. The controller 112 communicates with sensors 130 to monitor the pressure at which the suction 120 is operating at the applicator.

Controller 112 also operates the cooling elements 124 at the appropriate temperature as discussed above. The controller 112 communicates with sensors 130 to monitor the temperature at which the cooling elements 124 are cooling the tissue. The sensors 130 also monitor the temperature of the tissue for proper temperature management of the cooling elements 124.

The controller 112 also controls operation of the ultrasound waves applied to the tissue by the transducer 138. The controller 112 operates the transducer 138 at the proper treatment levels.

The controller 112 of one embodiment communicates with sensors 130 that monitor operation of different elements of the system. The sensors 130 monitor the temperature of the cooling elements, temperature of the tissue, pressure applied to the tissue via the suction 120, cooling of the outer side of the cooling elements, and the ultrasounds produced by transducer 138. The controller 112 communicates with the sensors 130 to maintain proper operation of the cooling of the tissue, applying the suction to the tissue, and applying the ultrasound waves to the tissue.

The user operates the system via touch screen 136 of the applicators and foot pedal 114. The user controls the cooling, suction, and ultrasound waves via the touchscreen 136 of the applicators and the foot pedal 114. In one embodiment, the touchscreen 136 displays information acquired by sensors 130. The touchscreen 136 displays the temperature of the tissue, the temperature of the cooling elements, the pressure of the suction on the tissue, and the operation of the ultrasounds. The touchscreen 136 also displays the elapsed time of the treatment.

In one embodiment, the operator activates/deactivates the applicators via a display, such as touchscreen 136, or other controls on the control unit or the applicators. Sensors on the applicators monitor the temperatures, pressure, and ultrasound applied by the applicators to the patient. The sensors monitor that the treatment is being properly applied to the patient. The display or touchscreen of one embodiment displays the information monitored by the sensors 130. Upon reaching the end of the treatment, the controller 112 shuts the applicators down to terminate the treatment.

In one embodiment, the user activates and deactivates the applicators via the foot pedal 114. By pressing the foot pedal 114, the user turns the applicators on to begin the treatment. The user can press the foot pedal 114 again or press and hold down the foot pedal 114 to turn the applicators off.

In one embodiment, the controller 112 alerts the user if the treatment conditions vary outside of the preferred treatment settings. The alert may be a visual alert, such as a light, strobe light, or message on the touchscreen 136, an audible alert, such as an alarm, or both a visual and audible alert.

Software 134 communicates with the touchscreen 136 and the controller 112 for the operation of the system. The software 136 enables adjustment of the settings for the treatment and provides information and alerts concerning the treatment.

The control unit, such as the housing, connects to a power source 116. The power source powers the controller 112 and the applicators. An isolation transformer 118 isolates the electrical components of the system. The system enables simultaneous use of two applicators that provide ultrasound and cooling simultaneously.

Figure 3:
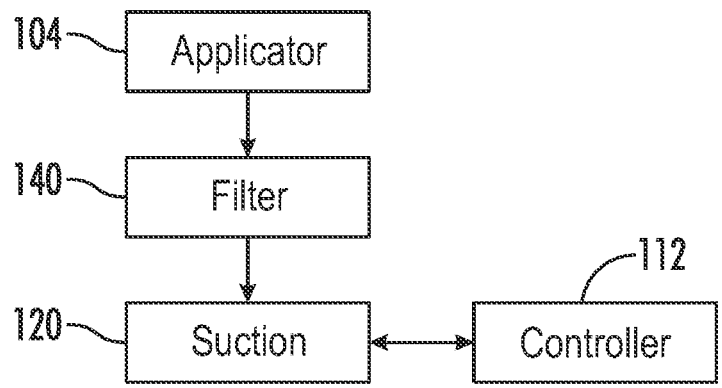
FIG. 3 is a schematic view of a suction of one embodiment of the present invention.

FIG. 3 shows the operation of the suction 120 by controller 112. The suction 120 draws the tissue into the applicator 104 to be cooled. In one embodiment, a treatment pad is placed between the tissue and the applicator such that the applicator does not directly contact the patient. The treatment pad is constructed from a fabric, such as a rayon and spandex fabric storing gel, deionized water, and fructose. Filter 140 protects the suction 120 from potential damage from the fluids, debris, and other materials that may be drawn into suction 120, including the fluids and gel from the treatment pad. The filter 140 directs the fluids, debris, and other materials to the suction receptacle.

Figure 4:
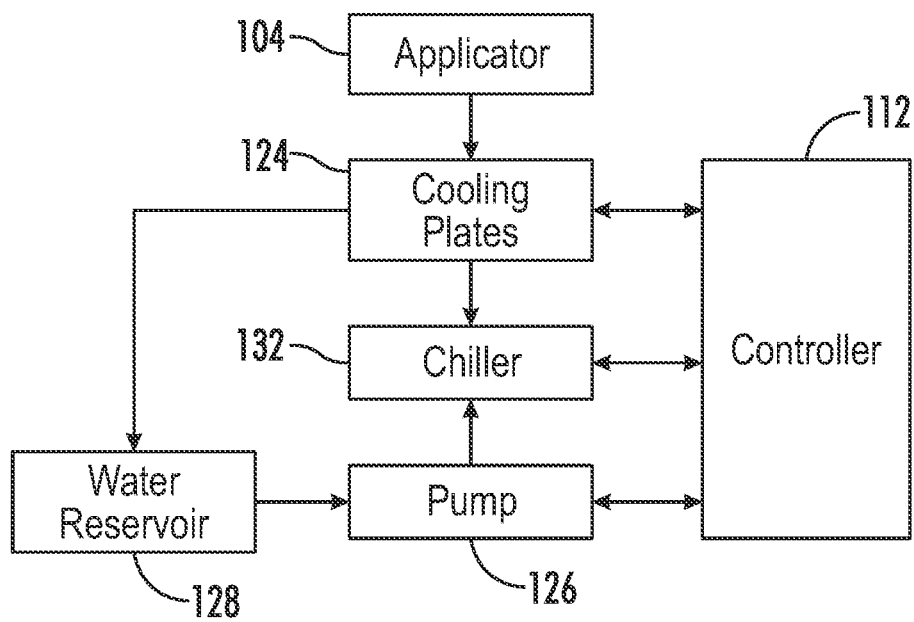
FIG. 4 is a schematic view of a cooling element of one embodiment of the present invention.

FIG. 4 shows operation of the cooling elements 124, such as the cooling plates, cooling aluminum plates. As the suction shown in FIG. 3 draws the tissue into the applicator 104, the cooling elements 124, such as the cooling plates, cool the tissue drawn into the applicator 104. In one embodiment, the cooling elements cool the tissue to a temperature ranging from −15 degrees Celsius to +10 degrees Celsius, preferably −11 degrees Celsius to +5 degrees Celsius. Controller 112 controls the temperature of the cooling elements 124, such as cooling plates or aluminum cooling plates. The user may modify the temperature via the touchscreen or other controls. In another embodiment, the controller 112 automatically changes the temperature of the cooling elements 124 for the proper treatment.

As discussed above, the cooling elements 124, such as cooling plates or aluminum plates, are thermoelectrically cooled. A heat sink is positioned adjacent the cooling elements 124. The controller 112 controls the pump 126 and chiller 132 that supplies fluid, such as water to the heat sink. The chilled water flows to the heat sink adjacent the cooling elements 124 to cool the cooling elements 124. In one embodiment, the fluid, such as the water, is stored in reservoir 128. The controller 112 may adjust the settings of the pump 126 and chiller 132 to cool the cooling elements 124 properly.

Figure 5:
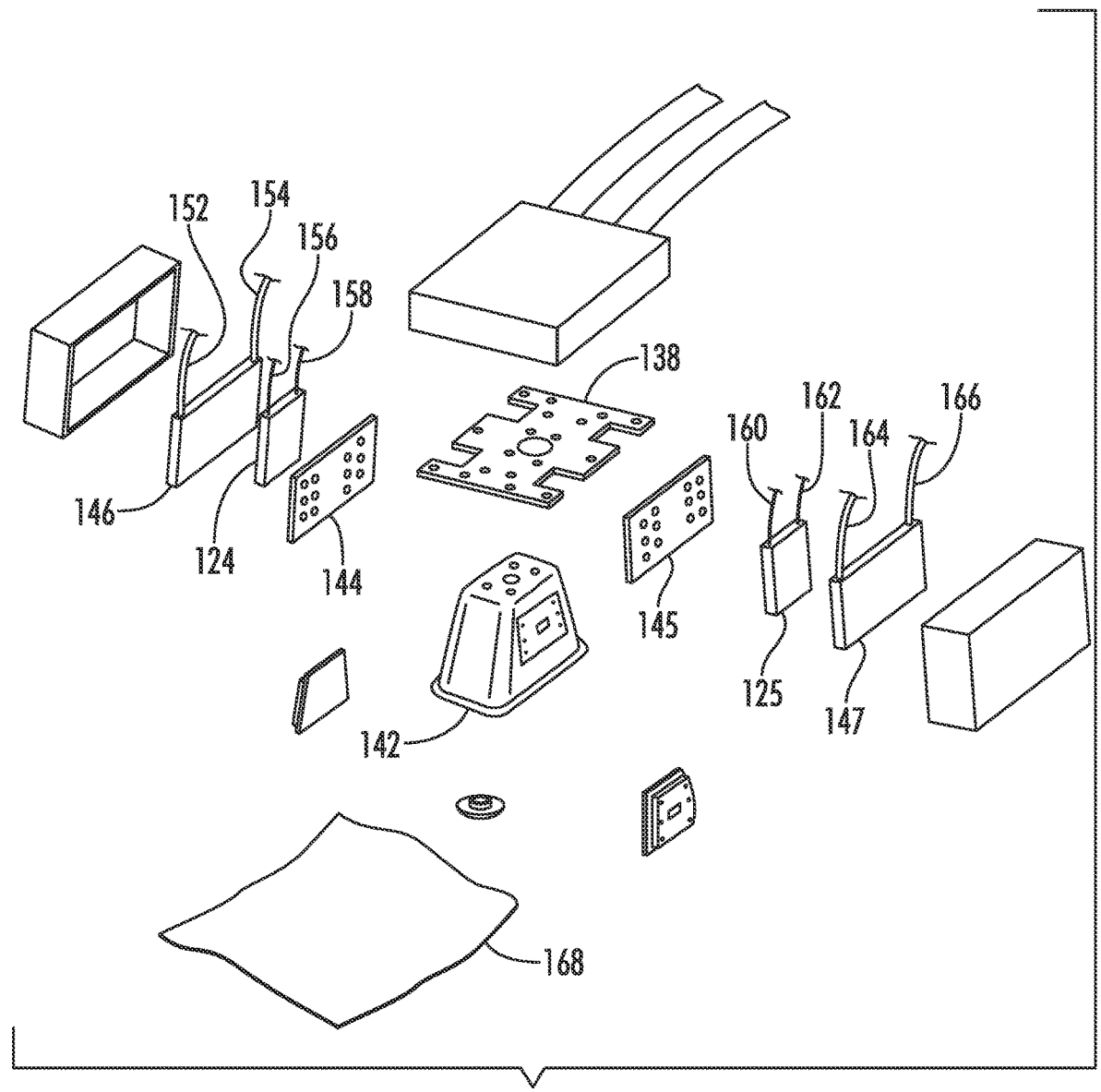
FIG. 5 is an exploded view of an applicator of one embodiment of the present invention.
Figure 6:
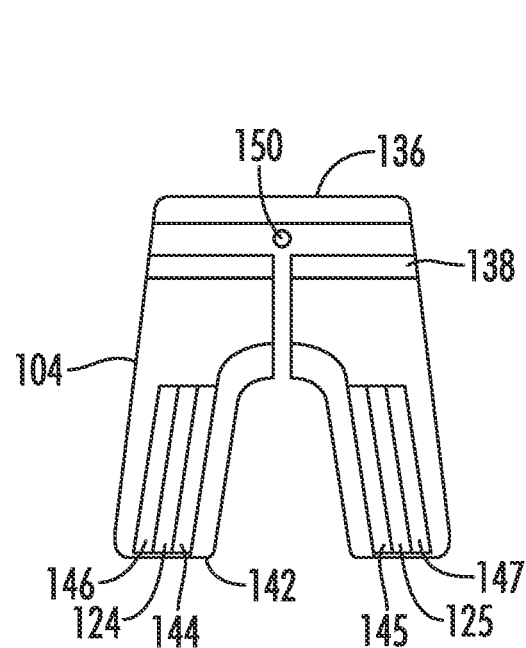
FIG. 6 is a sectional view of an applicator of one embodiment of the present invention.

FIGS. 5 and 6 show the applicator 104. Suction head 142 draws the tissue of the patient into cavity 148. The suction at the cavity 148 is formed by suction via suction port 150. The suction draws the tissue into the cavity 148 for cooling elements 124, 125, such as cooling plates, aluminum plates, or cooling aluminum plates, to cool the tissue drawn into cavity 148.

In one embodiment, the suction draws the tissue longitudinally into the cavity 148 of suction head 142. Supports 144, 145 provide support at the suction head 142. The supports 144, 145 provide apertures for attachment of the cooling elements 124, 125 and heat sinks 146, 147 with the suction head 142 of applicator 104. Supports 144, 145, cooling elements 124, 125 and heat sinks 146, 147 are located laterally outward from cavity 148.

The cooling elements 124, 125 cool the tissue in the cavity 148. Cooling elements 124, 125 are thermoelectrically cooled such that inner sides 127, 131 are cooled to a temperature ranging from −15 degrees Celsius to +10 degrees Celsius, preferably −11 degrees Celsius to +5 degrees Celsius.

Electrical connections 156, 158 of cooling plate 124 and electrical connections 160, 162 of cooling plate 125 provide electricity to the cooling elements 124, 125 for the thermoelectric cooling of the inner sides 127, 131 of the cooling elements 124, 125. The electrical connections 156, 158, 160, 162 connect to the housing and the power source.

The outer side 129, 133 is heated through the thermoelectric cooling of inner side 127, 131. In one embodiment, heat sinks 146, 147 are water cooled heat sinks. Water flows from the reservoir through the chiller into heat sinks 146, 147. The cooled water flowing from the chiller into the heat sinks 146, 147 cool the cooling elements 124, 125 and the outer side 129, 133 of cooling elements 124, 125.

Heat sinks 146, 147 cool the outer sides 129, 133 of the cooling elements 124, 125. Water connections 152, 154, 164, 166 provide a pathway for the cooling fluid, such as water, from the chiller to flow through the heat sinks 146, 147 to cool the cooling elements 124, 125. The water cooled heat sinks 146, 147 cool the outer side of the cooling elements 124, 125.

The applicator 104 also provides a transducer 138 for transmitting ultrasound waves at the tissue drawn longitudinally into the cavity 148. The transducer 138 is located longitudinally above the cavity. The suction in the applicator 104 draws the tissue longitudinally toward the transducer 138. The transducer 138 transmits ultrasound waves longitudinally downward into the cavity 148 at the tissue.

Figure 9:
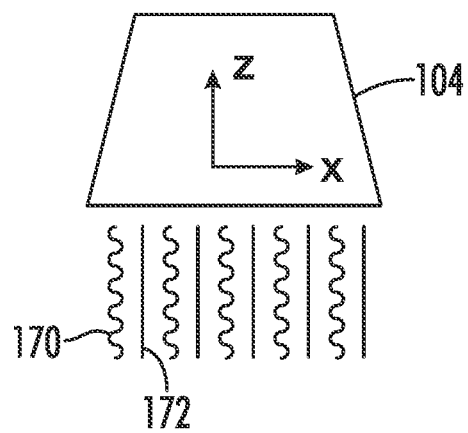
FIG. 9 is a front view of an applicator transmitting ultrasound waves of one embodiment of the present invention.
Figure 10:
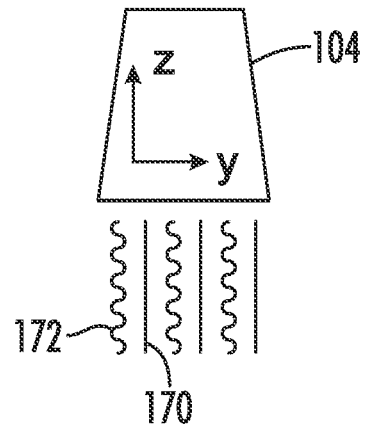
FIG. 10 is a left side view thereof.
Figure 11:
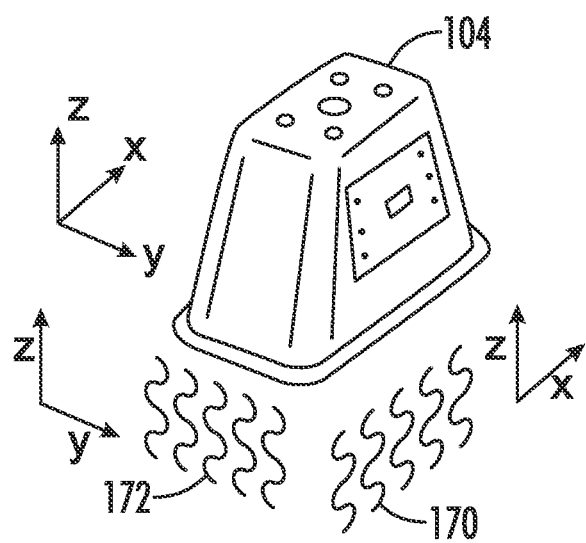
FIG. 11 is a perspective view thereof.

The transducer 138 transmits ultrasound waves in a first orientation that is not parallel with a second orientation. In one embodiment, the second orientation is perpendicular to the first orientation. In one embodiment, the ultrasound waves are oriented both vertically and horizontally at the tissue. The transmission of the ultrasound waves in different orientations at the tissue improves the treatment of the tissue as shown in FIGS. 9-11. FIGS. 9-11 show the different orientations of the ultrasound waves transmitted at the tissue drawn into the cavity 148.

Figure 7:
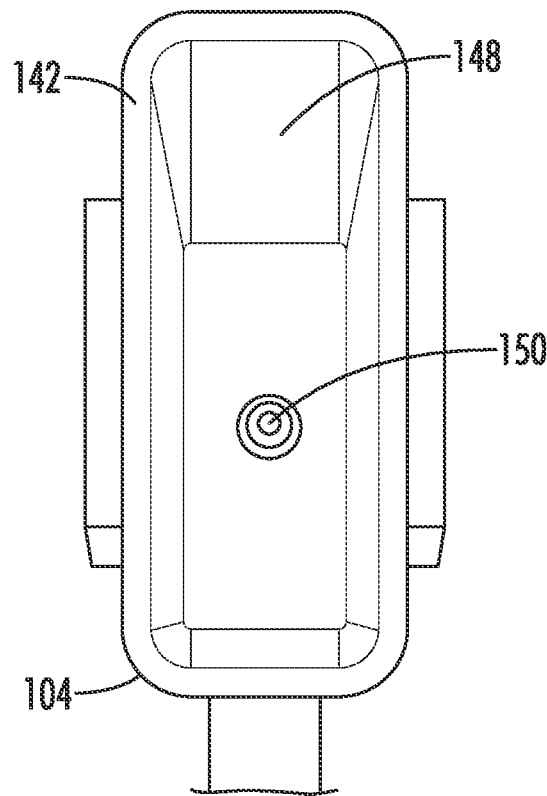
FIG. 7 is a bottom view thereof.

FIG. 7 shows a bottom view of the applicator 104. Suction port 150 draws the tissue longitudinally into the cavity 148 of the suction head 142. The transducer transmits the ultrasound waves longitudinally downward into the cavity 148.

Figure 8:
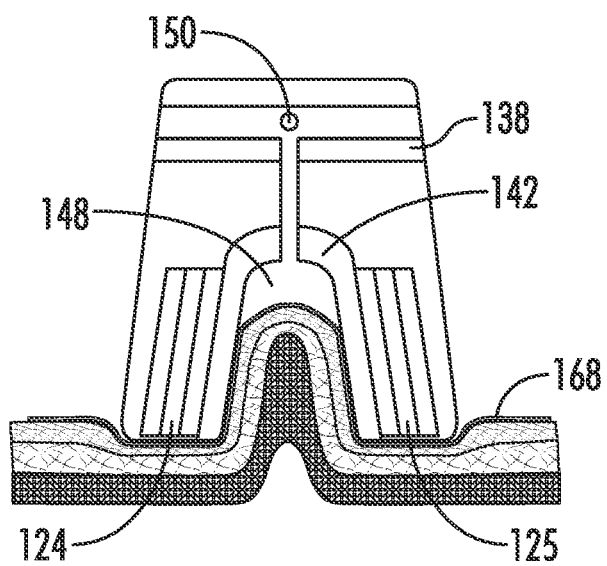
FIG. 8 is an environmental sectional view of one embodiment of the present invention.

FIG. 8. shows the use of the applicator 104 on the tissue. Suction draws the tissue of the patient into the suction head 142 of the applicator 104. Cooling elements 124, 125 cool the tissue drawn into the cavity 148. Prior to treatment, a person, such as a technician, user, or patient, places the pad 168 on the treated area. As discussed above, the treatment pad 168 is constructed from a fabric, such as a fabric constructed from spandex and rayon, storing a glycerin gel that is soaked in deionized water and fructose. The treatment pad 168 facilitates thermal contact and mitigates minor thermal variations. As shown in FIG. 8, the treatment pad 168 is positioned between the applicator and the tissue. Suction of the applicator 104 draws the tissue and the pad 168 into the cavity 148. Cooling elements 124, 125 cool the pad 168 and the tissue.

The present invention also provides a method of reducing fat cells within a patient's tissue. The skin must be prepared for treatment. The skin is cleaned at the treatment area with a skin cleaner. The thickness of the fat layer is measured. The treatment area is determined. The treatment area may be regionally divided if necessary. The technician or other operator then determines the treatment temperature and time for each region.

The treatment area is then covered with a treatment pad. The pad is constructed from a fabric, such as a fabric constructed from spandex and rayon, storing a glycerin gel, deionized water, and fructose. The treatment pad is positioned to cover the treatment area. If additional pads are needed, the pads are applied to the user's skin such that the pads do not overlap.

The applicator is then applied to the skin at the treatment pad. Suction draws the tissue into the cavity of the applicator. The applicator maintains the suction while the cooling plates cool the skin. The suction continues while the cooling plates continue to cool the tissue drawn into the cavity by the suction.

The applicators apply ultrasound waves to the tissue drawn into the applicator simultaneously with the cooling and the suction of the treated tissue. The applicators apply the ultrasound waves as the suction continues to draw the tissue into the cavity of the applicator and the cooling plates continue to cool the tissue drawn into the cavity of the applicator by the suction. The power density of the ultrasound is well below that of the recommended 3 W/cm^2 per IEC 60601-2-5:2009. The ultrasound is not audible to the human ear. The ultrasound is set by the operator. The operator may turn on the ultrasound at the housing or the touch screen display on the applicator.

The applicators transmit the ultrasound waves longitudinally downward into the cavity as shown in FIGS. 9-11. The ultrasound waves are transmitted intermittently for bursts ranging from 0.1 ms to 1 s during the last five (5) to ten (10) minutes of treatment. The transducer may transmit the ultrasound waves for a transmission period of 0.1 ms to is and have a delay period ranging from 0.1 ms to 5 s. The transducer alternates between transmitting ultrasound waves for the transmission period and delaying transmission (not sending) ultrasound waves for the delay period during the last five (5) to ten (10) minutes of the treatment.

During the last five (5) to ten (10) minutes of treatment, the tissue at the treatment area is drawn into the applicator, cooled by the cooling plates, and receives ultrasound waves simultaneously. Such treatment accelerates the apoptotic sequence and increase the metabolic absorption of the non-viable fat cells.

The ultrasound transmits the ultrasound waves in a first orientation and a second orientation. In one embodiment, the first orientation and the second orientation are not parallel with each other. In another embodiment, the first orientation is perpendicular to the second orientation as shown in FIGS. 9-11 such that the ultrasound waves are not parallel and intersect. In one embodiment, the ultrasound waves are directed horizontally and vertically. In one embodiment, the ultrasound waves 170, 172 are oriented 90 degrees in relation to each other. Ultrasound waves 170 are oriented in a first orientation perpendicular to ultrasound waves 172 oriented in a second orientation. The applicator 104 transmits different orientations of ultrasound waves 170, 172 to apply the ultrasound in different orientations to the fatty tissue.

The cooling system applies suction to the treatment area to draw the treated tissue into an applicator. The applicator provides suction, cooling, and ultrasound waves to simultaneously cool the tissue during suction of the tissue and transmitting ultrasound waves to the treated tissue simultaneously. The applicator transmits ultrasound waves in a first orientation and a second orientation that are not parallel to each other, such as perpendicular. The application of cooling and ultrasound waves while applying pressure caused by the suction to the tissue breaks down the fat cells within the tissue.

Further areas of applicability of the present invention will become apparent from the description provided hereinafter. It should be understood that the description and specific examples are intended for purposes of illustration only and are not intended to limit the scope of the present teachings.

From the foregoing, it will be seen that the present invention is one well adapted to obtain all the ends and objects herein set forth, together with other advantages which are inherent to the structure.

It will be understood that certain features and sub-combinations are of utility and may be employed without reference to other features and sub-combinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A cooling system for reducing fat cells within tissue of a patient, the system comprising:
   an applicator configured for cooling the tissue and applying ultrasound to the tissue of the patient;
   a cavity in the applicator configured to accept tissue drawn into the cavity, wherein an opening of the cavity is located at a first longitudinal end of the cavity;
   a suction connected to the applicator that creates a suction force into the cavity that suctions longitudinally into the cavity towards a second longitudinal end of the cavity opposite the opening, wherein the suction is configured to draw the tissue into the cavity towards the second longitudinal end;
   a suction opening located longitudinally between the cavity and the suction, wherein the suction opening and the suction are aligned longitudinally with the opening of the cavity;
   a first cooling element extending longitudinally between the suction opening and the opening of the cavity, wherein the first cooling element is located laterally outward from the cavity and applies a cooling effect laterally towards the cavity, wherein the first cooling element is configured to cool the tissue drawn into the cavity by the suction;
   a transducer located adjacent the cavity towards the second longitudinal end away from the opening, wherein the transducer extends laterally across the cavity, wherein the transducer applies ultrasound waves longitudinally into the cavity towards the opening, wherein the transducer is configured to apply ultrasound waves to the tissue drawn into the cavity by the suction;
   wherein the cooling effect is offset from the suction force and the ultrasound waves;
   wherein the suction force and application of the ultrasound waves are aligned;
   wherein the transducer transmits a first ultrasound wave of the ultrasound waves directed in a first orientation, wherein the first ultrasound wave has a wave height oriented in a first direction, wherein the transducer transmits the first ultrasound wave longitudinally into the cavity;
   wherein the transducer transmits a second ultrasound wave of the ultrasound waves in a second orientation wherein the second ultrasound wave has a wave height oriented in a second direction, wherein the transducer transmits the second ultrasound wave longitudinally into the cavity; and
   wherein the first direction is different than the second direction.

2. The system of claim 1, wherein the first direction is offset to the second direction.

3. The system of claim 1, wherein the first direction is perpendicular to the second direction.

4. The system of claim 1, wherein the first cooling element is an aluminum plate that is cooled by a thermoelectric cooler.

5. The system of claim 4 wherein the aluminum plate is cooled by water from a water source flowing across the aluminum plate.

6. The system of claim 1 further comprising:
   a second cooling element located laterally outward from the cavity that cools within the cavity, wherein the second cooling element is configured to cool the tissue drawn into the cavity by the suction, wherein the second cooling element is located opposite the cavity than the first cooling element, wherein the second cooling element applies a cooling effect laterally towards the cavity;
   wherein the ultrasound waves travel longitudinally through the cavity between the first cooling element and the second cooling element while the first cooling element and the second cooling element apply the cooling effects of the first cooling element and the second cooling element laterally into the cavity.

7. A cooling system for reducing fat cells within tissue of a patient, the system comprising:
   an applicator configured for cooling the tissue and applying ultrasound to the tissue of the patient simultaneously;
   a cavity in the applicator extending longitudinally into the applicator;
   an opening located at a first longitudinal end of the cavity, wherein the cavity is configured to accept tissue drawn into the opening of the cavity;
   a suction connected to the applicator that suctions longitudinally into the opening of the cavity towards a second longitudinal end of the cavity, wherein the suction is configured to draw the tissue longitudinally into the opening of the cavity;
   a first cooling element located laterally outward from the cavity, wherein the first cooling element cools within the cavity, wherein the first cooling element is configured to cool the tissue drawn into the cavity by the suction;
   a transducer located adjacent the cavity towards the second longitudinal end, wherein the transducer applies ultrasound waves longitudinally into the cavity from the second longitudinal end towards the first longitudinal end, wherein the transducer extends laterally across the cavity, wherein the transducer is configured to apply ultrasound waves to the tissue drawn into the cavity by the suction;
   wherein the ultrasound waves travel longitudinally through the cavity while the first cooling element applies a cooling effect laterally into the cavity;
   wherein the transducer transmits a first ultrasound wave of the ultrasound waves directed in a first orientation, wherein the first ultrasound wave has a wave height oriented in a first direction, wherein the transducer transmits the first ultrasound wave longitudinally into the cavity;
   wherein the transducer transmits a second ultrasound wave of the ultrasound waves directed in a second orientation, wherein the second ultrasound wave has a wave height oriented in a second direction; and
   wherein the first direction is offset from the second direction.

8. The system of claim 7, wherein the transducer extends laterally across the second longitudinal end of the cavity, wherein the second longitudinal end of the cavity is located longitudinally between the opening and the transducer.

9. The system of claim 8, wherein the transducer directs the ultrasound waves longitudinally downward toward the cavity.

10. The system of claim 9, wherein the first orientation is perpendicular to the second orientation.

11. The system of claim 7, wherein the first cooling element is an aluminum plate that is cooled by a thermoelectric process.

12. The system of claim 11 wherein the aluminum plate is cooled by a heat sink located laterally outward from the aluminum plate.

13. The system of claim 7 further comprising:
a second cooling element located laterally outward from the cavity, wherein the second cooling element cools within the cavity, wherein the second cooling element is configured to cool the tissue drawn into the cavity by the suction, wherein the second cooling element is located opposite the first cooling element, wherein the second cooling element applies a cooling effect laterally into the cavity;
wherein the ultrasound waves travel longitudinally through the cavity between the first cooling element and the second cooling element while the first cooling element and the second cooling element apply the cooling effects of the first cooling element and the second cooling element laterally into the cavity.

14. A cooling system for reducing fat cells within tissue of a patient, the system comprising:
an applicator configured for cooling the tissue and applying ultrasound to the tissue of the patient simultaneously;
a cavity formed by the applicator, wherein the cavity extends longitudinally into the applicator, wherein the cavity is configured to draw the tissue longitudinally into the cavity;
a suction connected to the applicator that suctions longitudinally into the cavity, wherein the suction is configured to draw the tissue longitudinally into the cavity;
a first cooling element located laterally outward of the cavity, wherein the first cooling element cools within the cavity, wherein the first cooling element is configured to cool the tissue drawn into the cavity by the suction;
a transducer located adjacent the cavity applying ultrasound waves into the cavity, wherein the transducer extends laterally across the cavity, wherein the transducer is configured to apply ultrasound waves to the tissue drawn into the cavity by the suction as the suction draws the tissue into the applicator, wherein the transducer directs the ultrasound waves longitudinally into the cavity;
wherein the transducer transmits a first ultrasound wave of the ultrasound waves directed in a first orientation, wherein the first ultrasound wave has a wave height oriented in a first direction, wherein the transducer transmits the first ultrasound wave longitudinally into the cavity;
wherein the transducer transmits a second ultrasound wave of the ultrasound waves directed in a second orientation, wherein the second ultrasound wave has a wave height oriented in a second direction; and
wherein the first direction is perpendicular to the second direction.

15. The system of claim 14, wherein the transducer transmits the ultrasound waves simultaneously in the first orientation and the second orientation.

16. The system of claim 15 further comprising:
a second cooling element located laterally outward from the cavity, wherein the second cooling element cools the cavity, wherein the second cooling element is configured to cool the tissue drawn into the cavity by the suction, wherein the second cooling element is located opposite the cavity than the first cooling element.

* * * * *